United States Patent [19]

Tomita et al.

[11] Patent Number: 5,314,873
[45] Date of Patent: May 24, 1994

[54] MILK-PROTEIN HYDROLYZATES AND COMPOSITIONS FOR USE AS HAIR AND SKIN TREATING AGENT

[75] Inventors: Mamoru Tomita, Yokohama; Takesi Kitazawa, Setagaya; Seiji Kawaura, Yotsukaido; Yasuo Fukuwatari, Kawasaki; Masanobu Nojiri, Machida, all of Japan

[73] Assignees: Morinaga Milk Industry Co., Ltd., Tokyo; Iwase Cosfa Co., Ltd., Ohsaka, both of Japan

[21] Appl. No.: 701,866

[22] Filed: May 17, 1991

[30] Foreign Application Priority Data

May 18, 1990 [JP] Japan .................................. 2-128363
May 18, 1990 [JP] Japan .................................. 2-128364

[51] Int. Cl.$^5$ ...................... A61K 37/02; C07K 1/12; C07K 3/10
[52] U.S. Cl. ...................... 514/21; 435/68.1; 530/343; 530/407; 530/832; 530/833
[58] Field of Search ............ 530/407, 343, 833, 832; 514/12, 2, 880, 21; 424/535; 435/68.1

[56] References Cited

U.S. PATENT DOCUMENTS

| | | | |
|---|---|---|---|
| 4,427,658 | 1/1984 | Maubois et al. | 424/177 |
| 4,463,017 | 7/1984 | Hidalgo et al. | 514/21 |
| 4,980,450 | 12/1990 | Brule et al. | 530/832 |
| 5,112,812 | 5/1992 | Samuelsson et al. | 514/21 |

FOREIGN PATENT DOCUMENTS

| | | |
|---|---|---|
| 48-43878 | 12/1973 | Japan . |
| 57-209210 | 12/1982 | Japan . |
| 58-500664 | 4/1983 | Japan . |
| 59-152317 | 8/1984 | Japan . |
| 60-258102 | 12/1985 | Japan . |
| 62-185100 | 8/1987 | Japan . |
| 62-61039 | 12/1987 | Japan . |
| 63-57515 | 3/1988 | Japan . |
| 64-11 | 1/1989 | Japan . |
| 1-269499 | 10/1989 | Japan . |
| 2-138991 | 5/1990 | Japan . |
| WO8203008 | 9/1982 | PCT Int'l Appl. . |

OTHER PUBLICATIONS

Translation of JA 2-138,991 (Published May 28, 1990).

*Primary Examiner*—Jeffrey E. Russel
*Attorney, Agent, or Firm*—Oblon, Spivak, McClelland, Maier & Neustadt

[57] ABSTRACT

A milk-protein hydrolyzate consisting of a mixture of peptides and free amino acids having proliferation activating property on human cutaneous cells but not having antigenicity of the milk-protein may be obtained by enzymatic hydrolysis of milk protein. The peptides of the hydrolyzate have molecular weights less than 1000 daltons, and the hydrolyzate has a free aromatic amino acid/total aromatic amino acid ratio of at least 90%. Fractionation of the milk protein hydrolyzate yields a fraction consisting of a mixture of peptides. The fraction has a proliferation activating property on human cutaneous cells but does not have the antigenicity of the milk protein. The fraction contains aromatic amino acids in an amount of less than 5% by weight of total amino acids. Both the hydrolyzate and the fraction can be formulated into cosmetic compositions for application to the hair and skin.

4 Claims, No Drawings

MILK-PROTEIN HYDROLYZATES AND COMPOSITIONS FOR USE AS HAIR AND SKIN TREATING AGENT

BACKGROUND OF THE INVENTION

1. Field of the Invention

The present invention relates to milk-protein hydrolyzate which is bereft of antigenicity of the milk-protein, which activates proliferation of human cutaneous cells, and which is effective for conditioning of hair and skin, and for prevention and recovery from damaged hair and skin. The present invention also relates to hair and skin treating composition such as cosmetic, non-drug and drug products (hereinafter these products shall be referred to as cosmetic and the like) consisting of or containing milk-protein hydrolyzate as the effective component.

2. Discussion of the Background

Heretofore, milk-protein and hydrolyzate thereof have been utilized in cosmetic and the like.

For example, Japanese Unexamined Patent Application Gazette No. 57(1982)-209210 discloses the utilization of amino acids, hydrochlorides of amino acids, alkaline salts of amino acids and peptides, inclusive of peptides originated from milk-protein, as an agent for increasing solubility of bis-(2-pyridylthio-1-oxide)-zinc which is antibacterial agent against dandruff.

Japanese Unexamined Patent Application Gazette published in Japanese language No. 58-500664 (corres. to International Application Gazette No. W082/03008; PCT/AU82/00022) discloses the utilization of polypeptide or protein inclusive of casein as a preventive agent against dental caries.

Japanese Unexamined Patent Application Gazette No. 59(1984)-152317 discloses the utilization of casein, casein hydrolyzate or a mixture thereof as a stabilizer to mutanase solution for preparation of a preventive agent against dental caries.

Japanese Unexamined Patent Application Gazette No. 63(1988)-57515 discloses a bath preparation containing macademian oil and peptide and/or amino acid obtainable by hydrolysis of milk-protein.

Japanese Unexamined patent Application Gazette No. 60(1985)-258102 discloses a hair and skin treating composition containing protein hydrolyzate as a protective agent for hair and skin, wherein the molecular weights of said hydrolyzate are made into 500-5000 for improvement in solubility of the hydrolyzate.

Japanese Unexamined Patent Application Gazette No. 62(1987)-185100 discloses a hair and skin treating composition containing polypeptide as a protective agent for hair and skin, emulsifier or emulsion-stabilizer for the composition, wherein the molecular weights are made into less than 26000 for minimizing stickiness of casein.

Japanese Unexamined Patent Application Gazette No. 64(1989)-11 discloses a method of preparation of a fraction of protein hydrolyzate to be used for an ingredient of cosmetic products, wherein the molecular weights of the hydrolyzate are made to 2000-200000 for eliminating problems of precipitation and/or turbidity in an aqueous solution of the hydrolyzate.

Japanese Unexamined Patent Application Gazette No. 1(1989)-269499 discloses a method of preparation of the peptide originated from casein for use as a hair and skin treating agent, wherein casein is hydrolyzed by trypsin and subtilisin for efficiently yielding peptides having molecular weights in the range of from 300 to 3000 which may improve solubility and chelatability of the peptides, stability of the peptides solution, adsorbability to hairs, affinity to hair and skin, protective property and moisturizing property, however, it does not prove the proliferation activating property of the peptides on human cutaneous cells.

The aims of addition of peptides to hair and skin treating compositions in these references are mainly for hair and skin conditioning effects such as moisturing, adsorbing, film forming and/or protective properties of the hydrolyzate.

In the prior art referred in the above, however, the effectiveness of peptide has not been proved, but merely relies upon rumor or belief. Furthermore there has been a problem that products containing peptide originating from milk protein may sometime cause a problem of allergy.

Some of the inventors of the present application have previously made an invention relating to hydrolyzate of milk-protein and a method of preparation of the same for the purposes of increase in solubility of milk-protein, increase in digestibility of milk-protein, prevention from or treatment of food allergy, treatment of or nutrition to patients having disorders in aromatic amino acids metabolism, and an application for patent for the invention has been filed in Japan by one of the assignees of the present invention (Japanese Patent Application No. 63(1988)-291090; filing date: Nov. 19, 1988 hereinafter this application will be referred to as the prior application.) The inventors of this application have conducted a thorough research with respect to the nature of the hydrolyzate of the prior application, and found that milk protein hydrolyzate having following natures can be used as a hair and skin treating agent or as an ingredient of hair and skin treating compositions: (a) said hydrolyzate is a mixture of peptides having molecular weights less than 1000 daltons; (b) 90% by weight or more of aromatic amino acids included in said mixture is free aromatic amino acids; (c) said mixture has a property to activate proliferation of human cutaneous cells; and (d) said mixture is bereft of antigenicity of the milk protein.

In other words, the inventors of the present invention found that when mi)k protein is hydrolized with two or more enzymes to a certain decomposition rate, the resultant hydrolyzate comprising a mixture of peptides having molecular weights less than 1000 daltons and 90% by weight or more of aromatic amino acids included in said mixture being free amino acids may surprisingly activate proliferation of human cutaneous cells, and is bereft of the antigenicity of the original milk protein, in addition to other properties as a hair and skin treating agent.

It was also found that a specific fraction of milk protein hydrolyzate having following natures can be used as the hair and skin treating agent or as an ingredient of hair and skin treating compositions: (a) said hydrolyzate is a mixture of peptides having molecular weigts less than 1000 daltons; (b) the percentage of aromatic amino acids to the whole amino acids included in the fraction is less than 5% by weight; (c) said mixture activate proliferation of human cutaneous cells; and (d) said mixture is bereft of antigenicity of the milk protein.

In other words, the inventors of the present invention found that peptides having the proliferation activating property on human cutaneous cells are included in a specific fraction of the milk protein hydrolyzate, said fraction being a mixture of peptides having molecular weights less than 1000 daltons, the aromatic amino acids included in said mixture being less than 5% by weight of the whole amino acids included in said mixture, said peptides being bereft of the antigenicity of the original milk protein and having other properties desirable as the hair and skin treating agent.

The present invention is based on these discoveries.

OBJECTS OF THE INVENTION

Therefore, it is an object of the present invention to provide milk-protein hydrolyzate, a fraction of the hydrolyzate or salts thereof, having proliferation promotion property on human cutaneous cells.

It is a further object of the present invention to provide milk-protein hydrolyzate, a fraction of the hydrolyzate or salts thereof which is bereft of antigenicity of the milk-protein.

It is another object of the present invention to provide milk-protein hydrolyzate consisting of a mixture of peptides having molecular weights less than 1000 daltons and amino acids, in which mixture 90% by weight or more of aromatic amino acids are free amino acids.

It is a further object of the present invention to provide a fraction of milk-protein hydrolyzate consisting of a mixture of peptides having molecular weights less than 1000 daltons, in which mixture aromatic amino acid is less than 5% by weight of the whole amino acids contained in the fraction.

It is a still further object of the present invention to provide hair and skin treating compositions containing milk protein hydrolyzate, a fraction of the hydrolyzate or salts thereof having proliferation promotion property on human cutaneous cells.

It is another object of the present invention to provide hair and skin treating compositions containing milk-protein hydrolyzate, a fraction of the hydrolyzate or salts thereof which is bereft of the antigenicity of the milk-protein.

It is another object of the present invention to provide hair and skin treating compositions comprising milk-protein hydrolyzate or salts thereof which has the following natures:

(a) said hydrolyzate consists of a mixture of peptides having molecular weights less than 1000 daltons and amino acids;

(b) the ratio of free aromatic amino acids to the whole aromatic amino acids in the mixture is greater than 90% by weight;

(c) said mixture activate proliferation of human cutaneous cells; and (d) said mixture is bereft of the antigenicity of the milk-protein.

It is a further object of the present invention to provide hair and skin treating composition comprising a fraction of milk-protein hydrolyzate or salts thereof which fraction has the following natures:

(a) said fraction consists of a mixture of peptides having molecular weights less than 1000 daltons and amino acids;

(b) the percentage of aromatic amino acids to the whole amino acids in said fraction is less than 5% by weight;

(c) said fraction activates proliferation of human cutaneous cells; and (d) said fraction is bereft of the antigenicity of the milk-protein.

It is a specific object of the present invention to provide milk protein hydrolyzate, a fraction of milk protein hydrolyzate, or salts thereof which activate proliferation of human cutaneous cells and which are used as the hair and skin treating agent or as an ingredient of hair and skin treating compositions.

SUMMARY OF THE INVENTION

In accordance with one aspect of the present invention, milk-protein hydrolyzate or salts thereof consisting of a mixture of peptides which activate proliferation of human cutaneous cells is provided in a higher yield by enzymatic hydrolysis of milk-protein, and which can be used as a hair and skin treating agent or an ingredient of hair and skin treating compositions. The peptides included in said mixture have molecular weights less than 1000 daltons and are substantially bereft of the antigenicity of the original milk protein, and 90% by weight of aromatic amino acids in said mixture is free aromatic amino acids.

In accordance with the other aspect of the present invention, a fraction comprising a mixture of peptide which may activate proliferation of human cutaneous cells is provided in a higher yield by fractionation of said milk protein hydrolyzate or salts thereof, and which can be used as a hair and skin treating agent or as an ingredient of hair and skin treating compositions. The peptides included in said fraction have molecular weights less than 1000 daltons and are substantially bereft of the antigenicity of the original milk protein, and aromatic amino acids included in said fraction is 5% by weight of the whole amino acids therein.

DETAILED DESCRIPTION OF THE INVENTION

Any milk-proteins sold in the market such as casein, or its fractions (e.g. $\alpha_3$-casein, $\beta$-casein, $\gamma$-casein and $\kappa$-casein), and whey-protein or its fractions (e.g. $\alpha$-lact albumin and $\beta$-lact globulin), and a mixture thereof can be used as the source of the hydrolyzate (hereinafter they are referred to as milk-proteins). They are subjected to enzymatic hydrolysis in the form of aqueous solution in a proper concentration, e.g. between 5 and 20%.

The enzymes to be used for the hydrolysis are not limited, for example, trypsin, chymotrypsin, subtilisin, elastase, papain, pepsin, thermolycin, prolin-specific protease, carboxypeptidase Y, pancreatin, and other proteases produced by the microorganisms belonging to the genus of Streptococcus, Aspergilus, Streptomyces, Rhizopus and lactic acid bacteria or extract of lactic acid bacteria can be used. The extract of lactic acid bacteria can be prepared, for example, in accordance with the method disclosed in Japanese Examined Patent Application No. 48(1973)-43878 in an activity of 20000 unit per gram. It is preferable to use two or more different types of enzymes in combination, for example, a combination of endopeptidase and exopeptidase, or a combination of pancreatin, exopeptidase and one or more of other proteases.

In general, one or more of enzymes can be used in a quantity from 3000–5000 units per gram of the protein, however, the quantity is not limited thereto. When two or more of enzymes are to be used, they can be added to the protein solution in a mixture thereof or alternatively they are individually added at a proper interval for stepwise hydrolysis by the different enzymes.

Hydrolysis can be carried out under a temperature between 40°-55° C., and pH of the protein solution is adjusted to a pH value which is closer to the optimum pH values of the enzymes to be used and which should eliminate denaturation of the proteins. Preferably the enzymatic hydrolysis is made while the solution is kept at the pH at least for one hour from the initiation of the hydrolysis.

After proper reaction period, enzymes are deactivated by heating, and if necessary, the resultant reaction mixture is cooled, filtered, demineralized, concentrated, and/or dried to obtain the hydrolyzate in a liquid or powdery form.

The resultant hydrolyzate activates proliferation of human cutaneous cells, and has substantially none of the antigenicity of the milk-protein, and furthermore 90% by weight or more of aromatic amino acids contained in the hydrolyzate are made into free amino acids and the constituent peptides have molecular weights less than 1000 daltons.

The resultant hydrolyzate can be subjected to fractionation, for example, gel-filtration or hydrophobic-chromatography to obtain a fraction in which aromatic amino acids are less than 5% by weight of the whole amino acids. The peptides included in the fraction have molecular weights less than 1000 daltons, and are substantially bereft of the antigenicity of the original milk protein, and activate proliferation of human cutaneous cells. For example, aqueous solution of the resultant hydrolyzate is poured into a column filled with gel having exclusion limit of molecular weight less than 10000 daltons, preferably less than 1000 daltons, more preferably gel having adsorbing property to aromatic amino acids and having hydrophobic side-chains such as carboxyl, buthyl, phenyl groups or hydrophobic cites (for example, Sephadex G-10, G-15,and G-25 by Pharmacia, Sephacryl S-100 by Pharmasia, TOYOPEARL HW-40 by Tosoh and the like), then eluted with 0-15% ethanol solution for increasing adsorption property of aromatic amino acids. Fractionation is made based on 280 nm absorbancy.

Depending upon the gel used, 4 or 3 elution peaks can be observed, wherein 1st elution peak in the latter case correspond to 1st and 2nd elution peaks in the former (which are hereinafter referred to as elution peaks A and B). 2nd and 3rd elution peaks of the latter case correspond to 3rd and 4th elution peaks in the former (which are referred to as elution peaks C and D). In either instances, elution peaks C and D are not suited for preparation of the hair and skin treating compositions of the present invention, since they are rich in aromatic amino acids, and they are not easily soluble into water. Therefore, a fraction consisting of elution peaks A and-/or B is utilized in the other aspect of the present invention. The fraction can be condensed and/or dried to obtain concentrated solution or powder of the fraction.

The resultant hydrolyzate or the fraction can be added to prepare cosmetic and the like in the conventional manner in the art, for example, the hydrolyzate is dissolved into water, then the resultant solution is mixed with other ingredients of the cosmetic and the like, emulsified or suspended therein. The hydrolyzate is easily soluble in water in a concentration up to 20%. and solubility is decreased as the concentration increased.

The salts of the hydrolyzate or its fractions may be organic and inorganic salts as far as they are acceptable in preparation of drug, non-drug and cosmetic products.

If required, emulsifier, perfumery and any other components which are acceptable as the ingredients of drug, non-drug and cosmetic products can be added to the hydrolyzate, fractions or salts thereof, as far as they are compatible therewith.

Now some exemplifying tests will be described hereunder.

TEST 1

The purpose of this test is to determine the physico-chemical natures of the milk-protein hydrolyzates.

(1) PREPARATION OF MILK PROTEIN HYDROLYZATES (1—1) CASEIN HYDROLYZATE

A solution containing an extract of lactic acid bacteria, protease originated from Aspergillus and pancreatin in the same ratio in activity unit was prepared. To a 10% aqueous casein solution (pH 8.0). the resultant enzyme solution was added in 3000 activity units/g of the protein. The resultant mixture was subjected to hydrolysis at 50° C. During the hydrolysis, decomposition rate of casein was periodically measured by formol titration. At each time when the decomposition rate of casein in the mixture reached to 21, 32, and 41%, a part of the mixture was taken out and heated at 90° C. for 5 minutes for deactivation of the enzymes. After deactivation, each part of the mixture was filtered until precipitate is completely removed, then each of the resultant filtrates was lyophilized to thereby obtain 3 kinds of test samples, A, 8 and C.

(1-2) WHEY PROTEIN HYDRLOYZATE

A 10% aqueous whey protein solution (pH 7.0) was hydrolyzed in the same manner as in (1—1) to thereby obtain two kinds of test samples (lyophilized whey protein hydrolyzate), D (decomposition rate 30%) and E (decomposition rate 41%) were obtained.

(2) ANALYSIS OF AMINO ACIDS

The contents of amino acids and free aromatic amino acids in each of the samples A-E were measured by automatic amino acid analyzer (hereinafter the contents of whole amino acids will be abbreviated as WA, the contents of whole aromatic amino acids will be abbreviated as Ar, and the contents of free aromatic amino acids will be abbreviated as FAr). Then Ar/WA ratio, FAr/WA ratio and the percentage of FAr/Ar were calculated. The results are shown in Table 1 together with the respective decomposition rates.

As is apparent from Table 1, the ratios of FAr/Ar increased as the decomposition rates increased. It is also apparent that the percentage of FAr/Ar of samples C and E are greater than 90%.

For the purpose of comparison, a control sample (sample F) of casein hydrolyzate having average molecular weight of 1000 daltons was prepared in accordance with Example 1 of Japanese Unexamined Patent Application Gazette No. 1(1989)-269499 (hereinafter abbreviated as JUPAG 1-269499), and the percentage of FAr-/Ar of the control sample F was less than 90% by weight.

MEASUREMENT OF MOLECULAR WEIGHTS

The molecular weights of samples C and E prepared in the above item (1) were measured using Sephadex G-25 column and eluting solution of 0.5N acetic acid. It was determined that the molecular weights of samples C and E are less than 1000 daltons, since the 1st fraction of the samples C and E were eluted later than oxytocin (molecular weight 1000 daltons) which was used as the reference.

TEST 2

The purpose of this test is to determine the antigenicity of the samples A-E and control sample F by ELISA inhibition test.

Plates each having 96 wells (sold by Nunc) were respectively coated with either of casein or whey protein, then washed for removal of unfixed proteins. On the other hand, rabbit anti-casein antiserum and rabbit anti-whey-protein antiserum were respectively reacted with each of the corresponding samples A-E and control sample F for antigen-antibody reaction. The resultant reaction mixtures were respectively poured into wells coated with the corresponding proteins for reaction between the fixed proteins and the corresponding rabbit antisera which were remained in the respective reaction mixtures, then washed for removal of unfixed matters. Goat anti-rabbit IgG antibody labelled with alkaline phosphate (sold by Zymed Laboratories) was poured into the respective wells for fixation thereof to the rabbit antiserum which was fixed to the fixed proteins, then washed for removal of unfixed labelled antibody. Sodium p-nitrophenyl-phosphate which is the substrate to said enzyme was added to each well for enzymatic reaction for 30 minutes. The enzymatic reaction was terminated by addition of 5N sodium hydroxide to each well, then the reaction products in the wells were measured by a microplate reader (450 nm) (cf. Journal of the Medical Society of Toho University, Vol. 35, No. 6, Page 509-516, 1989). As the results, it was determined that antigenicity of the hydrolyzate samples is reduced as the FAr/Ar ratio increased. More particularly, antigenicity of sample A (31% FAr/Ar ratio) and sample B (57% FAr/Ar ratio) were respectively 1/400 and 1/30000 of that of casein, and antigenicity of sample C (greater than 90% FAr/Ar ratio) was almost disappeared. Similarly, antigenicity of sample E (greater than 90% FAr/Ar ratio) was disappeared. However, antigencity of control sample F (less than 90% FAr/Ar ratio) was apparently remained as 1/320.

TEST 3

The purpose of this test is to determine the proliferation activating property of milk protein hydrolyzate on human cutaneous cells.

Comparative tests were made with respect to sample C prepared in Test 1, commercial bovine placenta extract (sold by Boettger of Germany) and sample F prepared in accordance with Example 1 of JUPAG 1-269499 as follows.

Human epithelial cells and fibroblasts were respectively incubated in accordance with the conventional method in modified KGM culture medium and modified KGM culture medium containing 2% of bovine fetal serum respectively. The resultant culture media were respectively divided into twelve parts, to each of which were added sample C, bovine placenta extract and sample F respectively in the ratios of 0 (control), 1, 10 and 100 µg/ml. After 2-3 days incubation, $^3$H labelled thymidine was added to the respective culture broths, then incubated further for 2-3 hours, then the quantities of $^3$H taken into the cells were measured by a liquid scintillation counter.

The results are shown in Table 2.

As is seen from Table 2, sample C shows remarkable proliferation activating effect with respect to both of human epithelial cells and fibroblasts.

In contrast to this, effects of bovine placenta extract and sample F are not corelated to the added quantity thereof. Moreover, with respect to the efficacy of bovine placenta extract on fibroblasts, the resulted values show apparently negative efficacy.

TEST 4

The purpose of this test is to determine the effects of hair and skin treating compositions with or without inclusion of milk-protein hydrolyzate of the present invention.

(1) PREPARATION OF SAMPLES

Seven test samples (test sample Nos. 1-7) and seven control samples (control samples A-G) of hair and skin treating compositions were prepared with the ingredients shown hereunder in accordance with the conventional method. Note that the ingredients of test samples Nos. 1-7 respectively correspond to those of Examples Nos. 1-7 infra, and that those of control samples A-G correspond to test sample Nos. 1-7, substituting milk protein hydrolyzate in test sample Nos. 1-7 with water.

| SKIN CREAM | | |
|---|---|---|
| | test sample No. 1 (%) | control sample A (%) |
| stearic acid | 15.0 | 15.0 |
| cetyl alcohol | 2.0 | 3.0 |
| squalane | 3.0 | 3.0 |
| 2-octyldodecyl myristate | 5.0 | 5.0 |
| glycerol | 10.0 | 10.0 |
| 1,3-butylen glycol | 4.0 | 4.0 |
| polyoxyethylene (20) sorbitan monostearate | 3.0 | 3.0 |
| milk protein hydrolyzate of Reference Method 1 | 5.0 | 0 |
| purified water | 53.0 | 58.0 |

| TOILET WATER | | |
|---|---|---|
| | test sample No. 2 (%) | control sample B (%) |
| propylene glycol | 10.0 | 10.0 |
| oleyl alcohol | 0.1 | 0.1 |
| polyoxyethylene (60) hydrogenated castor oil | 1.5 | 1.5 |
| ethyl alcohol | 5.0 | 5.0 |
| milk protein hydrolyzate of Reference Method 1 | 3.5 | 0 |
| purified water | 79.9 | 83.4 |

| COLOGNE WATER | | |
|---|---|---|
| | test sample No. 3 (%) | control sample C (%) |
| sodium hyaluronate | 0.1 | 0.1 |
| placenta extract | 1.5 | 1.5 |
| glycerol | 1.0 | 1.0 |
| milk protein hydrolyzate of Reference Method 2 | 4.0 | 0 |
| purified water | 93.4 | 97.4 |

| OINTMENT FOR EPIDAMIS | | |
|---|---|---|
| | test sample | control sam- |

-continued

|  | No. 4 (%) | ple D (%) |
|---|---|---|
| petrolatum white | 25.0 | 25.0 |
| paraffin wax | 5.0 | 5.0 |
| cetostearyl alcohol | 2.0 | 2.0 |
| propylene glycol | 10.0 | 10.0 |
| polyoxyethylene polyoxypropylene glycol ether | 3.0 | 3.0 |
| milk protein hydrolyzate of Reference Method 1 | 5.0 | 0 |
| purified water | 50.0 | 55.0 |

HAIR TREATMENT LOTION

|  | test sample No. 5 (%) | control sample E (%) |
|---|---|---|
| cetyl alcohol | 1.5 | 1.5 |
| 2-hexyldecanol | 1.0 | 1.0 |
| 1,3-butylene glycol | 3.0 | 3.0 |
| hydroxyethylcellulose hydroxypropyl trimethyl ammonium chloride ethel | 0.2 | 0.2 |
| polyoxyethylene stearyl ether | 1.0 | 1.0 |
| milk protein hydrolyzate of Reference Method 2 | 4.0 | 0 |
| purified water | 89.3 | 93.3 |

HAIR RINSE

|  | test sample No. 6 (%) | control sample F (%) |
|---|---|---|
| dialkyl dimethyl ammonium chloride | 2.0 | 2.0 |
| cetyl alcohol | 1.0 | 1.0 |
| polyoxyethylene stearyl ether | 1.0 | 1.0 |
| 1,3-butylene glycol | 3.0 | 3.0 |
| hydroxyethylcellulose hydroxypropyl trimethyl ammonium chloride ethel | 0.2 | 0.2 |
| milk protein hydrolyzate of Reference Method 1 | 4.5 | 0 |
| purified water | 88.3 | 92.8 |

HAIR SHAMPOO

|  | test sample No. 7 (%) | control sample G (%) |
|---|---|---|
| triethanolamine lauryl sulfate | 15.0 | 15.0 |
| 1,3-buthylene glycol | 2.0 | 2.0 |
| ethyleneglycol monostearate | 1.5 | 1.5 |
| milk protein hydrolyzate of Reference Method 2 | 5.0 | 0 |
| purified water | 76.5 | 81.5 |

(2) METHOD

(2-1) TESTS OF SKIN TREATING COMPOSITIONS

Five professional panelists (20th–40th ages) who have apparently roughened skin were selected. Having cleaned the inner side of their left arms with commercial toilet soap, and ascertained that no soap was left, 0.5 g of test sample Nos. 1–4 and corresponding control samples A–D were applied and rubbed into their skin at the different spots of 30 mm × 15 mm in size. This treatment was continued once a day for 4 consecutive weeks, and evaluation was done once a week ion the following items in accordance with the following criteria with the naked eyes and the sense of touch.

items:
prevention from progress in roughening of the skin
recovery from the roughened skin
smoothness of the skin
regularity of ridges and furrows of the skin
elasticity of the skin
softness of the skin
protection of the skin
criterion:

| considerably better than control | +2 |
|---|---|
| somewhat better than control | +1 |
| no difference | 0 |
| somewhat worse than control | −1 |
| considerably worse than control | −2 |

Mean values were calculated from the evaluation in the respective items.

(2—2) TESTS OF HAIR TREATING COMPOSITIONS

Fifteen professional panelists (20th–40th ages) who have apparently damaged, dry and roughened hair were divided into three groups for the tests on samples No. 5 and E (hair treatment lotion, group 1), on samples No. 6 and F (hair rinse, group 2) and on samples No. 7 and G (hair shampoo, group 3).

In the case of groups 1 and 2, 2 g of the assigned samples (hair treatment lotion and hair rinse) were applied and rubbed every 4 days into their hair on the opposite side regions (about 50 mm × 80 mm) on their heads, after their hairs were sufficiently cleaned with commercial shampoo and sufficiently washed with water so that no shampoo was remained. In the case of group 2 in which hair rinse samples were to be tested, their hairs were lightly washed with water after application of the samples. This treatment was repeated 10 times, and evaluation was made every 4 days before the treatment.

In the case of group 3 in which shampoo samples were to be tested, the panelists' hair on the opposite side of their heads were separately cleaned with assigned test and control samples without using commercial shampoo then washed with water until no shampoo was detected. This hair wash was made once a day for 15 consecutive days. Evaluation was made every day before washing on the following items in accordance with the following criteria with the naked eyes and the sense of touch.

items:
recovery from the damaged hairs
prevention from the snapping and/or splitting hairs
softness of the hairs
smoothness after the hair caring
recovery from the dry and roughened hairs
brightness of the hairs
criterion:

| considerably better than control | +2 |
|---|---|
| somewhat better than control | +1 |
| no difference | 0 |
| somewhat worse than control | −1 |
| considerably worse than control | −2 |

Mean values were calculated from the evaluation in the respective items.

(3) RESULTS

The results of this test are shown in Tables 3 and 4.

It was confirmed that sample Nos. 1 and 2 are effective, in comparison with control samples A and B, for recovery from the roughened skin in all of the 5 panelists, and effective for improvement in elasticity of the skin in 4 of the 5 panelists.

It was confirmed that sample No. 3 is effective, in comparison with control sample C, for recovery from the roughened skin, improvement in regularity of ridges and furrows of the skin and smoothness of the skin in 4 of the 5 panelists.

It was confirmed that sample No. 4 is effective, in comparison with control sample D, for recovery from the roughened skin in all of the 5 panelists, and is effective for improvement in smoothness of the skin in 4 of the 5 panelists.

It was confirmed that sample No. 5 is effective, in comparison with control sample E, for recovery from damaged hair and from the dry and roughened hair in 4 of the 5 panelists.

It was confirmed that sample No. 6 is effective, in comparison with control sample F, for recovery from damaged hair and softening of the hair in all of the 5 panelists, and is effective for improvement in smoothness after the hair caring and recovery from the dry and roughened hair in 4 of the 5 panelists.

It was confirmed that sample No. 7 is effective, in comparison with control sample G, for recovery from damaged hair, improvement in smoothness after the hair caring and recovery from the dry and roughened hair in 4 of the 5 panelists.

Therefore, it was exemplified that the addition of the milk protein hydrolyzate of the present invention in various hair and skin treating compositions is significantly effective.

TEST 5

The purpose of this test is to determine the preferable concentration of milk protein hydrolyzate to be added to hair and skin treating compositions.

(1) PREPARATION OF SAMPLES

Test samples of skin cream and hair treatment lotion were prepared with the corresponding ingredients as in Examples 1 and 5 (infra) respectively, except that the percentage of milk protein hydrolyzate to be added was varied within the range of 0.01-50% and that the percentage of purified water to be added was varied to compensate the variation in the percentage of the former. Control samples of skin cream and hair treatment lotion containing no milk protein hydrolyzate were prepared with the same ingredients as in control samples A and E of Test 4 (supra).

(2) METHOD

This test was carried out by the same method as used in Test 4 supra, however, items for evaluation were restricted to as follows:
with respect to skin cream:
recovery from progress in the roughened skin,
prevention from roughening of the skin, and
elasticity of the skin,
with respect to hair treatment lotion:
recovery from the damaged hairs
prevention from snapping and/or splitting of the hairs

(3) RESULTS

The results are shown in Table 5.

In general, effects of the hydrolyzate were remarkably noted with respect to the skin creams and hair treatment lotions. The effects increased as the percentage of the added hydrolyzate increased up to 10%, the effects reached to the maximum at 10-20%, and lowered at 30-50%.

Therefore, it was determined that the preferable percentage of milk protein hydrolyzate to be added is less than 20%, more preferably between 0.01-20%.

TEST 6

The purpose of this test is to determine the preferable percentage of the hydrolyzate to be added to other products except for those tested in Test 5 supra.

(1) PREPARATION OF SAMPLES

Test samples of toilet water, cologne water, ointment for epidermis, hair rinse and hair shampoo were prepared with the corresponding ingredients as indicated in Examples 2, 3, 4, 6, and 7 infra respectively, except that the percentage of milk protein hydrolyzate was varied within the range of 0.01, 20 and 50% and that the percentage of purified water was varied to compensate the variation in the percentage of the former. Control samples of the corresponding products containing no milk protein hydrolyzate were also prepared with the same ingredients as in control samples B, C, D, F and G of Test 4 supra.

(2) METHOD

The method was the same as in Test 5 infra.

(3) RESULTS

The results of this test are shown in Table 6.

As is apparent from Table 6, it was confirmed that preferable percentage of the milk protein hydrolyzate to be added to skin and hair treating compositions was 0.01-20%.

Now a typical method for hydrolysis of milk protein will be described hereunder just for reference.

REFERENCE METHOD 1

Into a quantity of water, 200 g of commercial casein was dissolved to make a 10% aqueous casein solution, pH of the resultant solution was adjusted to 8.0 with a 10% aqueous sodium hydroxide solution. After sterilization at 90° C. for 10 minutes, the resultant solution was cooled to 45° C., 10 g of Pancreatin F (by Amano Pharmaceutical Co., Ltd.), 2 g of Protease N AMANO (by Amano Pharmaceutical Co., Ltd.) and 4 g of the extract from lactic acid bacteria were added to the solution, the resultant mixture was hydrolyzed at 45° C. for 24 hours. The resultant mixture was heated at 90° C. for 5 minutes to deactivate the enzymes, then the mixture was filtered until precipitate could not observed. The resultant filtrate was lyophilized to thereby obtain about 165 g of powdery casein hydrolyzate.

It was confirmed that the percent of FAr/Ar of the resultant casein hydrolyzate was 90.5% by weight, that antigenicity of the casein was substantially bereft, that the molecular weights of peptides included in the casein hydrolyzate were less than 1000 daltons, and proliferation activating property on human cutaneous cells was observed in similar extent by the same methods as in Tests 1, 2 and 3 supra.

REFERENCE METHOD 2

Into a quantity of water, 200 g of commercial whey protein powder was dissolved to make an 8% aqueous whey protein solution, pH of the resultant solution was adjusted to 7.5 with a 5% aqueous sodium hydroxide solution. The resultant solution was sterilized by a filter system, then the temperature of the solution was adjusted to 45° C. While the pH of the solution was maintained at 7.5 with a 5% aqueous sodium hydroxide solution, hydrolysis of the solution was performed for 15 hours with adding Pancreatin F (by Amano Pharmaceutical Co., Ltd.). in 6 times by 2 g at 30 minutes interval, then the resultant solution was further hydrolyzed with adding 2.0 g of Actinase AS (by Kaken Seiyaku) for 5 hours at the same temperature. The resultant solution was heated at 90° C. for 5 minutes to deactivate the enzymes and filtered. Then the filtrate was subjected to lyophilization thereby about 160 g of whey protein hydrolyzate powder was obtained.

It was confirmed that the percentage of FAr/Ar of the resultant whey protein hydrolyzate was 90.4% by weight, that antigenicity of the whey protein was substantially bereft, that the molecular weights of the peptides included in the hydrolyzate were less than 1000 daltons, and that proliferation activating property on human cutaneous cells was observed in a similar extend by the same methods as in Tests 1, 2 and 3 supra.

Now some embodiments of hair and skin treating compositions containing milk protein hydrolyzate will be described hereunder for better understanding of the present invention. Since the compositions were prepared in accordance with the conventional method, the list of the ingredients thereof will be suffice for the embodiments.

EXAMPLE 1

Skin cream was prepared in accordance with the conventional method with the following ingredients.

| SKIN CREAM | |
|---|---|
| stearic acid | 15.0 (%) |
| cetyl alcohol | 2.0 |
| squalane | 3.0 |
| 2-octyldodecyl myristate | 5.0 |
| glycerol | 10.0 |
| 1,3-butylene glycol | |
| polyoxyethylene (20) sorbitan monostearate | 3.0 |
| milk protein hydrolyzate of Reference Method 1 | 5.0 |
| purified water | 53.0 |

EXAMPLE 2

Toilet water was prepared in accordance with the conventional method with the following ingredients.

| propylene glycol | 10.0 (%) |
|---|---|
| oleyl alcohol | 0.1 |
| polyoxyethylene (60) hydrogenated castor oil | 1.5 |
| ethyl alcohol | 5.0 |
| milk protein hydrolyzate of Reference Method 1 | 3.5 |
| purified water | 79.9 |

EXAMPLE 3

Cologne water was prepared in accordance with the conventional method with the following ingredients.

| sodium hyaluronate | 0.1 (%) |
|---|---|
| placenta extract | 1.5 |
| glycerol | 1.0 |
| milk protein hydrolyzate of Reference Method 2 | 4.0 |
| purified water | 93.4 |

EXAMPLE 4

Ointment for epidermis was prepared in accordance with the conventional method with the following ingredients.

| petrolatum white | 25.0 (%) |
|---|---|
| paraffin wax | 5.0 |
| cetostearyl alcohol | 2.0 |
| propylene glycol | 10.0 |
| polyoxyethylene polyoxypropylene glycol ether | 3.0 |
| milk protein hydrolyzate of Reference Method 1 | 5.0 |
| purified water | 50.0 |

EXAMPLE 5

Hair treatment lotion was prepared in accordance with the conventional method with the following ingredients.

| cetyl alcohol | 1.5 (%) |
|---|---|
| 2-hexyldecanol | 1.0 |
| 1,3-butylene glycol | 3.0 |
| hydroxyethylenecellulose hydroxypropyl trimethyl ammonium chloride ether | 0.2 |
| polyoxyethylene stearyl ether | 1.0 |
| milk protein hydrolyzate of Reference Method 2 | 4.0 |
| purified water | 89.3 |

EXAMPLE 6

Hair rinse was prepared in accordance with the conventional method with the following ingredients.

| dialkyl dimethyl ammonium chloride solution | 2.0 (%) |
|---|---|
| cetyl alcohol | 1.0 |
| polyoxyethylene stearyl ether | 1.0 |
| 1,3-butylene glycol | 3.0 |
| hydroxyethylenecellulose hydroxypropyl trimethyl ammonium chloride ether | 0.2 |
| milk protein hydrolyzate of Reference Method 1 | 4.5 |
| purified water | 88.3 |

EXAMPLE 7

Hair shampoo was prepared in accordance with the conventional method with the following ingredients.

| triethanolamine lauryl sulfate solution | 15.0 (%) |
|---|---|
| 1,3-buthylene glycol | 2.0 |
| ethyleneglycol monostearate | 1.5 |
| milk protein hydrolyzate of Reference Method 2 | 5.0 |
| purified water | 76.5 |

Now some tests with respect to the fraction of milk protein hydrolyzate will be described hereunder.

TEST 7

The purpose of this test is to determine the physicochemical nature of the fractions of milk protein hydrolyzate.

(1) PREPARATION OF FRACTIONS OF MILK PROTEIN HYDROLYZATE

(1—1) FRACTIONS OF CASEIN HYDROLYZATE

Casein hydrolyzate was prepared by the same method as in Reference Method 1 supra.

To a quantity of water, 16 g of the resultant powdery casein hydrolyzate was dissolved to prepare a 20% aqueous casein hydrolyzate solution. The resultant hydrolyzate solution was poured into a column filled with Sephadex G-10 (10×12cm), then eluted with deionized water at a flow rate of 10 ml/minute. The eluate was fractionated based on absorption at 280 nm into 1st, 2nd, 3rd and 4th elution peaks. The respective fractions were lyophilized to thereby obtain about 8.7 g, about 4.9 g, about 1.6 g and about 0.3 g of the powdery fractions A-D.

(1-2) FRACTIONS OF WHEY PROTEIN HYDROLYZATE

Whey protein hydrolyzate was prepared by the same method as in Reference Method 2 supra.

To a quantity of water, 100 g of the hydrolyzed whey protein was dissolved to prepare a 10% aqueous whey protein hydrolyzate solution, the resultant solution was poured into a column filled with Sephadex G-10 (37×15 cm), then eluted with deionized water at a flow late of 200 ml/minute. The eluate was fractionated based on absorption at 280 nm into 1st, 2nd, 3rd and 4th elution peaks. The respective fractions were lyophilized to thereby obtain about 54 g, about 33 g, about 8 g and about 1.5 g of the powdery fractions of whey protein hydrolyzate E-H.

(2) ANALYSIS OF AMINO ACIDS

The contents of each amino acids in each of the fractions A-H were measured by automatic amino acid analyzer, then the ratios of Ar/WA was calculated therefrom.

The results of the analysis are shown in Table 7.

As is seen from Table 7, the percentage of Ar/WA of fractions A, B, E and F were less than 5% by weight, on the other hand the percentage of Ar/WA of fractions C, D, G and H were as high as more than 40% and solubility thereof were as low as 2%. The percentage of Ar/WA of casein peptide of average molecular weight of 1000 daltons prepared in accordance with Example 1 of JUPAG 1-269499 (control) was greater than 5% by weight.

(3) MEASUREMENT OF MOLECULAR WEIGHTS

The molecular weights of fractions A and E were measured using Sephadex G-25 column and elution liquid of 0.5M acetic acid solution. As the results, the 1st elution peaks of fractions A and E were eluted after oxytocin (molecular weight of 1000 daltons) which was used as the reference substance, thus the molecular weights of fractions A-D and E-H were confirmed to be less than 1000 daltons.

TEST 8

The purpose of this test is to determin the antigenicities of the fractions A, B, E and F of the milk protein hydrolyzates prepared in Test 7 by ELISA inhibition test.

The method of ELISA inhibition test was the same as Test 2 supra.

As the results, it was determined that the antigenicities of the fractions A, B, E and F were lowered to $1/10^5$ of that of the corresponding milk proteins. From the results, it was concluded that the antigenicities of fractions A, B, E and F were substantially bereft.

TEST 9

The purpose of this test is to determine the proliferation activating property of the fractions of milk protein hydrolyzate on human cutaneous cells.

Proliferation activating property of fractions A, B, prepared in Test 7, commercial bovine placenta extract (sold by Boettger of Germany) and sample I prepared in accordance with Example 1 of JUPAG 1-269499 on human cutaneous cells was tested by the same method as Test 3 in supra.

The results are shown in Table 8.

As is seen from Table 8, fractions A and B showed remarkable proliferation activating effect with respect to both of human epitherial cells and fibroblasts.

Though the effect of sample I on human epithelial cells seemed to correlate with the added quantity thereof, however, the effect at the addition of 1 μg/ml was negative (compare the values at the added quantities of 0 and 1 μg/ml thereof). The effect of bovine placenta extract on human epithelial cells and the effects of control sample I on human fibroblasts were not correlated to the added quantities thereof. With respect to the effect of bovine placenta extract on human fibroblasts, the resulted values showed apparently negative effect. Similar results were obtained with respect to fractions E and F.

TEST 10

The purpose of this test is to determine the effects of hair and skin treating compositions with or without inclusion of fractions of milk-protein hydrolyzate of the present invention.

(1) PREPARATION OF SAMPLES

Fourteen test samples (test sample Nos. 8-21) and seven control samples (control samples J-P) of hair and skin treating compositions were prepared with the ingredients shown hereunder in accordance with the conventional method. Note that the ingredients of test sample Nos. 8-21 respectively correspond to those of Examples Nos. 8-infra, in such a manner that successive two test samples, i.e. test samples pairs 8 and 9, 10 and 11, 12 and 13, 14 and 15, 16 and 17, 18 and 19, and 20 and 21 correspond to Example Nos. 8-14. The ingredients of the control samples J-P also correspond to said pairs of test sample Nos. 8-21, wherein fractions of milk protein hydrolyzate in the corresponding test sample Nos. 8-21 were substituted with water.

| SKIN CREAM | | |
|---|---|---|
| test sample No. 8 (%) | test sample No. 9 (%) | control sample J (%) |

-continued

| | | | |
|---|---|---|---|
| stearic acid | 15.0 | 15.0 | 15.0 |
| cetyl alcohol | 2.0 | 2.0 | 2.0 |
| squalane | 3.0 | 3.0 | 3.0 |
| 2-octyldodecyl myristate | 5.0 | 5.0 | 5.0 |
| glycerol | 10.0 | 10.0 | 10.0 |
| 1,3-butylene glycol | 4.0 | 4.0 | 4.0 |
| polyoxyethylene (20) sorbitan monostearate | 3.0 | 3.0 | 3.0 |
| fraction A of Reference Method 3 | 5.0 | 0 | 0 |
| fraction B of Reference Method 3 | 0 | 5.0 | 0 |
| purified water | 53.0 | 53.0 | 58.0 |

TOILET WATER

| | test sample No. 10 (%) | test sample No. 11 (%) | control sample K (%) |
|---|---|---|---|
| propylene glycol | 10.0 | 10.0 | 10.0 |
| oleyl alcohol | 0.1 | 0.1 | 0.1 |
| polyoxyethylene (60) hydrogenated castor oil | 1.5 | 1.5 | 1.5 |
| ethyl alcohol | 5.0 | 5.0 | 5.0 |
| fraction A of Reference Method 3 | 3.5 | 0 | 0 |
| fraction B of Reference Method 3 | 0 | 3.5 | 0 |
| purified water | 79.9 | 79.9 | 83.4 |

COLOGNE WATER

| | test sample No. 12 (%) | test sample No. 13 (%) | control sample L (%) |
|---|---|---|---|
| sodium hyaluronate | 0.1 | 0.1 | 0.1 |
| placenta extract | 1.5 | 1.5 | 1.5 |
| glycerol | 1.0 | 1.0 | 1.0 |
| fraction E of Reference Method 4 | 4.0 | 0 | 0 |
| fraction F of Reference Method 4 | 0 | 4.0 | 0 |
| purified water | 93.4 | 93.4 | 97.4 |

OINTMENT FOR EPIDAMIS

| | test sample No. 14 (%) | test sample No. 15 (%) | control sample M (%) |
|---|---|---|---|
| Petrolatum white | 25.0 | 25.0 | 25.0 |
| paraffin wax | 5.0 | 5.0 | 5.0 |
| cetostearyl alcohol | 2.0 | 2.0 | 2.0 |
| propylene glycol | 10.0 | 10.0 | 10.0 |
| polyoxyethylene polyoxypropylene glycol ether | 3.0 | 3.0 | 3.0 |
| fraction A of Reference Method 3 | 5.0 | 0 | 0 |
| fraction B of Reference Method 3 | 0 | 5.0 | 0 |
| purified water | 50.0 | 50.0 | 55.0 |

HAIR TREATMENT LOTION

| | test sample No. 16 (%) | test sample No. 17 (%) | control sample N (%) |
|---|---|---|---|
| cetyl alcohol | 1.5 | 1.5 | 1.5 |
| 2-hexyl decanol | 1.0 | 1.0 | 1.0 |
| 1,3-butylene glycol | 3.0 | 3.0 | 3.0 |
| hydroxyethylcellulose hydroxypropyl trimethyl ammonium chloride ether | 0.2 | 0.2 | 0.2 |
| polyoxyethylene stearyl ether | 1.0 | 1.0 | 1.0 |
| fraction E of Reference Method 4 | 4.0 | 0 | 0 |
| fraction F of Reference Method 4 | 0 | 4.0 | 0 |
| purified water | 89.3 | 89.3 | 93.3 |

HAIR RINSE

| | test sample No. 18 (%) | test sample No. 19 (%) | control sample O (%) |
|---|---|---|---|
| dialkyl dimethyl ammonium chloride | 2.0 | 2.0 | 2.0 |
| cetyl alcohol | 1.0 | 1.0 | 1.0 |
| polyoxyethylene stearyl ether | 1.0 | 1.0 | 1.0 |
| 1,3-butylene glycol | 3.0 | 3.0 | 3.0 |
| hydroxyethylcellulose hydroxypropyl trimethyl ammonium chloride ether | 0.2 | 0.2 | 0.2 |
| fraction A of Reference Method 3 | 4.5 | 0 | 0 |
| fraction B of Reference Method 3 | 0 | 4.5 | 0 |
| purified water | 88.3 | 88.3 | 92.8 |

HAIR SHAMPOO

| | test sample No. 20 (%) | test sample No. 21 (%) | control sample P (%) |
|---|---|---|---|
| triethanolamine lauryl sulfate solution | 15.0 | 15.0 | 15.0 |
| 1,3-buthylene glycol monostearate | 2.0 | 2.0 | 2.0 |
| ethyleneglycol monostearate | 1.5 | 1.5 | 1.5 |
| fraction E of Reference Method 4 | 5.0 | 0 | 0 |
| fraction F of Reference Method 4 | 0 | 5.0 | 0 |
| purified water | 76.5 | 76.5 | 81.5 |

(2) METHOD (2-1) TESTS OF SKIN TREATING COMPOSITIONS

Five professional panelist (20th–40th ages) who have apparently roughed skin were selected. Having cleaned the inner side of their left and right arms with commercial toilet soap, and ascertained that no soap was left, 0.5 g of test sample Nos. 8–11 and corresponding control samples J and K were applied on their left arms and rubbed into their skin at the different spots of 30 mm × 15 mm in size, and 0.5 g of test sample Nos. 12–15 and corresponding control samples L and M were applied on their right arms and rubbed into their skin at the different spots of 30 mm × 15 mm in size. This treatment wa continued once a day for 4 consecutive weeks, and evaluation was done once a week on the following items in accordance with the following criteria with the naked eyes and the sense of touch.

items:
prevention from progress in roughening of the skin
recovery from the roughened skin
smoothness of the skin
regularity of ridges and furrows of the skin
elasticity of the skin
softness of the skin
protection of the skin
criterion:

| | |
|---|---|
| considerably better than control | +2 |
| somewhat better than control | +1 |
| no difference | 0 |
| somewhat worse than control | −1 |
| considerably worse than control | −2 |

Mean values were calculated from the evaluation in the respective items.

(2—2) TESTS OF HAIR TREATING COMPOSITIONS

Thirty professional panelists (20th–40th ages) who have apparently damaged, dry and roughened hairs were divided into 6 groups each consists of 5 panelists for the tests on samples No. 16 and N (group 4, hair treatment), on samples No. 17 and N (group 5, hair treatment), on samples No. 18 and O (group 6, hair rinse), on samples No. 19 and O (group 7, hair rinse), on samples No. 20 and P (group 8, hair shampoo), and on samples No. 21 and P (group 9, hair shampoo).

In the case of groups 4–7, 2 g of the assigned samples were applied and rubbed every 4 days into their hairs on the opposite side regions (about 50 mm×80 mm) on their heads, after their hairs were sufficiently cleaned with commercial shampoo and sufficiently washed with water so that no shampoo is remained. In the case of groups 6 and 7 in which hair rinse samples were to be tested, the hairs of panelists were lightly washed with water after the application of the assigned samples. This treatment was repeated 10 times and evaluation was made every 4 days before the treatment.

In case of groups 8 and 9 in which hair shampoo samples were to be tested, the panelists hairs on the opposite side of their heads were separately cleaned with assigned test and control samples without using commercial shampoo, then washed with water until no shampoo is detected. This hair wash was made once a day for 15 consecutive days, and evaluation was made every day before washing on the following items in accordance with the following criteria with the naked eyes and the sense of touch.

items:
recovery from the damaged hairs
prevention from the snapping and/or splitting hairs
softness of the hairs
smoothness after the hair caring
recovery from the dry and roughened hairs
brightness of the hairs
criterion:

| | |
|---|---|
| considerably better than control | +2 |
| somewhat better than control | +1 |
| no difference | 0 |
| somewhat worse than control | −1 |
| considerably worse than control | −2 |

Mean values were calculated from the evaluation in the respective items.

(3) RESULTS

The results of this test are shown in Tables 9 and 10.

It was confirmed with respect to skin treating compositions that test samples in which fraction A or E was added were effective for recovery from roughened skin and improvement elasticity, and test samples in which fraction B or F was added were effective for recovery from roughened skin.

With respect to hair treating compositions, test samples in which fraction A or E was added were effective for recovery from damaged hairs and improvement in smoothness after caring, and test samples in which fraction B or F was added were effective for recovery from damaged hair.

Therefore, it was exemplified that the addition of the fractions of the milk protein hydrolyzate of the present invention in various hair and skin treating compositions is significantly effective.

TEST 11

The purpose of this test is to determine the preferable concentration of the fractions of milk protein hydrolyzate to be added to hair and skin treating compositions.

(1) PREPARATION OF SAMPLES

Test samples of skin cream and hair treatment lotion were prepared with the corresponding ingredients as in Examples 8, 9, 16 and 17 (infra) respectively, except that the percentage of the fraction of milk protein hydrolyzate to be added was varied within the range of 0.01–50% and that the percentage of purified water to be added was varied to compensate the variation in the percentage of the former. Control samples of skin cream and hair treatment lotion containing no fraction of milk protein hydrolyzate were prepared with the same ingredients as in control samples J and N of Test 10 (supra).

(2) METHOD

This test was carried out by the same method as used in Test 10 supra, however, items for evaluation were restricted to as follows:
with respect to skin cream:
recovery from the roughened skin,
with respect to hair treatment:
recovery from the damaged hairs

(3) RESULTS

The results are shown in Table 11.

In general, effects of the hydrolyzate fraction were remarkably noted with respect to the skin creams and hair treatment lotions. The effects increased as the percentage of the added hydrolyzate fraction increased up to 5%. the effects reached to the maximum at 5–20%, and lowered at 30–50%. The percentage of the addition of hydrolyzate fractions are preferable to be less than 20%, more preferably 0.01–20%.

TEST 12

The purpose of this test is to determine the preferable percentage of the hydrolyzate fractions to be added to other products except for those tested in Test 11, supra.

(1) PREPARATION OF SAMPLES

Test samples of toilet water, cologne water, ointment for epidermis, hair rinse and hair shampoo were prepared with the corresponding ingredients as indicated in Examples 10–15, and 18–21 (infra) respectively, except that the percentage of fractions of milk protein hydrolyzate was varied within the range of 0.01, 1.0, 20, 30 and 50%, and that the percentage of purified water was varied to compensate the variation in the percentage of the former. Control samples of the corresponding products containing no milk protein hydrolyzate were also prepared with the same ingredients as in samples K, L, M, O and P of Test 10 supra.

(2) METHOD

The method was the same as in Test 11 infra.

(3) RESULTS

The results of this test are shown in Table 12.

As is apparent from Table 12, it was confirmed that preferable percentage of fractions of he milk protein hydrolyzate to be added to skin and hair treating compositions was 0.01–20%.

Now typical method for preparation of fractions of milk protein hydrolyzate will be described hereunder just for reference.

REFERENCE METHOD 3

Into a quantity of water, 200 g of commercial casein was dissolved to make a 10% aqueous casein solution, pH of the resultant solution was adjusted to 8.0 with a 10% aqueous sodium hydroxide solution. After sterilization at 90° C. for 10 minutes, the resultant solution was cooled to 45° C., then 10 g of Pancreatin F (by Amano Pharmaceutical Co., Ltd.), 2 g of Protease N AMANO (by Amano Pharmaceutical Co., Ltd.) and 4 g of the extract from lactic acid bacteria were added to the solution, the resultant mixture was subjected to hydrolysis at 45° C. for 24 hours. After enzymatic hydrolysis, the solution was heated at 90 for 5 minutes for deactivation of the enzymes, then the resultant solution was filtered for removal of precipitate. The resultant filtrate was lyophilized to thereby obtain about 165 g of powdery casein hydrolyzate.

It was confirmed by the same methods as in Tests 7, 8 and 9 supra that the percentage of FAr/Ar of the resultant casein hydrolyzate was 90.5% by weight, and that antigenicity of the casein was substantially bereft.

To a quantity of water, 16 g of the resultant milk protein hydrolyzate was dissolved to prepare a 20% aqueous casein hydrlyzate solution, the resultant solution was poured into Sephadex G-10 column (10×12 cm), then eluted with deionized water at a flow rate of 10 ml/minute. The resultant eluate was fractionated based on absorption at 280 nm into 1st, 2nd, 3rd and 4th elution peaks. The respective fractions were lyophilized to thereby obtain about 8.7 g, about 4.9 g, about 1.6 g and about 0.3 g of powdery fractions of casein hydrlyzate (fractions A-D).

REFERENCE METHOD 4

Into a quantity of deionized water, 200 g of commercial whey protein powder was dissolved to make an 8% aqueous casein solution, the resultant solution was sterilized by a filter system, then the temperature of the solution was adjusted to 45° C. While the pH of the solution was maintained at 7.5 with a 5% aqueous sodium hydroxide solution, hydrolysis of the solution was performed for 15 hours with adding Pancreatin F (by Amano Pharmaceutical Co., Ltd.) in 6 times by 2 g at 30 minutes interval, then the resultant solution was further subjected to hydrolysis by adding 2.0 g of Actinase AS (by Kaken Seiyaku) for 5 hours at the same temperature. The resultant solution was heated at 90° C. for 5 minutes for deactivation of the enzymes, then subjected to filtration for removal of the precipitate, the resultant filtrate was subjected to lyophilization thereby about 160 g of whey protein hydrolyzate powder was obtained.

It was confirmed by the same methods as in Tests 7. 8 and 9 supra that the percentage of FAr/Ar of the resultant whey protein hydrolyzate was 90.4%. and that antigenicity of the whey protein was substantially bereft.

To a quantity of water, 100 g of the resultant whey protein hydrolyzate was dissolved to prepare a 10% aqueous whey protein hydrolyzate solution, the resultant solution was poured into Sephadex G-10 column (37×15 cm), then eluted with deionized water at a flow rate of 200 ml/minute. The resultant eluate was fractionated based on absorption at 280 nm into 1st, 2nd, 3rd and 4th elution peaks. The respective fractions were lyophilized to thereby obtain about 54 g, about 33 g, about 8 g and about 1.5 g of the powdery fractions of whey protein hydrolyzate (fractions E-H).

Now some embodiments of hair and skin treating compositions containing a fraction of milk protein hydrolyzate will be described hereunder for better understanding of the present invention. Since the compositions were prepared in accordance with the conventional method, listing of the ingredients thereof will be suffice for the embodiments.

EXAMPLE 8

Skin cream was prepared in accordance with the conventional method with the following ingredients.

| stearic acid | 15.0 (%) |
|---|---|
| cetyl alcohol | 2.0 |
| squalane | 3.0 |
| 2-octyldodecyl myristate | 5.0 |
| glycerol | 10.0 |
| 1,3-butylene glycol | 4.0 |
| polyoxyethylene (20) sorbitan monostearate | 3.0 |
| fraction A of Reference Method 3 | 5.0 |
| purified water | 53.0 |

EXAMPLE 9

Skin cream was prepared in accordance with the conventional method with the following ingredients.

| stearic acid | 15.0 (%) |
|---|---|
| cetyl alcohol | 2.0 |
| squalane | 3.0 |
| 2-octyldodecyl myristate | 5.0 |
| glycerol | 10.0 |
| 1,3-butylene glycol | 4.0 |
| polyoxyethylene (20) sorbitan monostearate | 3.0 |
| fraction B of Reference Method 3 | 5.0 |
| purified water | 53.0 |

EXAMPLE 10

Toilet water was prepared in accordance with the conventional method with the following ingredients.

| propylene glycol | 10.0 (%) |
|---|---|
| oleyl alcohol | 0.1 |
| polyoxyethylene (60) hydrogenated castor oil | 1.5 |
| ethyl alcohol | 5.0 |
| fraction A of milk protein hydrolyzate of Reference Method 3 | 3.5 |
| purified water | 79.9 |

EXAMPLE 11

Toilet water was prepared in accordance with the conventional method with the following ingredients.

| propylene glycol | 10.0 (%) |
|---|---|
| oleyl alcohol | 0.1 |
| polyoxyethylene (60) hydrogenated castor oil | 1.5 |
| ethyl alcohol | 5.0 |
| fraction B of milk protein | 3.5 |

EXAMPLE 12

Cologne water was prepared in accordance with the conventional method with the following ingredients.

| | |
|---|---|
| sodium hyaluronate | 0.1 (%) |
| placenta extract | 1.5 |
| glycerol | 1.0 |
| fraction E of milk protein | 4.0 |
| hydrolyzate of Reference Method 4 | |
| purified water | 93.4 |

EXAMPLE 13

Cologne water was prepared in accordance with the conventional method with the following ingredients.

| | |
|---|---|
| sodium hyaluronate | 0.1 (%) |
| placenta extract | 1.5 |
| glycerol | 1.0 |
| fraction F of milk protein | 4.0 |
| hydrolyzate of Reference Method 4 | |
| purified water | 93.4 |

EXAMPLE 14

Ointment for epidermis was prepared in accordance with the conventional method with the following ingredients.

| | |
|---|---|
| petrolatum white | 25.0 (%) |
| paraffin wax | 5.0 |
| cetostearyl alcohol | 2.0 |
| propylene glycol | 10.0 |
| polyoxyethylene polyoxypropylene glycol ether | 3.0 |
| fraction A of milk protein | 5.0 |
| hydrolyzate of Reference Method 3 | |
| purified water | 50.0 |

EXAMPLE 15

Ointment for epidermis was prepared in accordance with the conventional method with the following ingredients.

| | |
|---|---|
| petrolatum white | 25.0 (%) |
| paraffin wax | 5.0 |
| cetostearyl alcohol | 2.0 |
| propylene glycol | 10.0 |
| polyoxyethylene polyoxypropylene glycol ether | 3.0 |
| fraction B of milk protein | 5.0 |
| hydrolyzate of Reference Method 3 | |
| purified water | 50.0 |

EXAMPLE 16

Hair treatment lotion was prepared in accordance with the conventional method with the following ingredients.

| | |
|---|---|
| cetyl alcohol | 1.5 (%) |
| 2-hexyldecanol | 1.0 |
| 1,3-butylene glycol | 3.0 |
| hydroxyethylenecellulose hydroxypropyl trimethyl ammonium chloride ether | 0.2 |
| polyoxyethylene stearyl ether | 1.0 |
| fraction E of milk protein | 4.0 |
| hydrolyzate of Reference Method 4 | |
| purified water | 89.3 |

EXAMPLE 17

Hair treatment lotion was prepared in accordance with the conventional method with the following ingredients.

| | |
|---|---|
| cetyl alcohol | 1.5 (%) |
| 2-hexyldecanol | 1.0 |
| 1,3-butylene glycol | 3.0 |
| hydroxyethylenecellulose hydroxypropyl trimethyl ammonium chloride ether | 0.2 |
| polyoxyethylene stearyl ether | 1.0 |
| fraction F of milk protein | 4.0 |
| hydrolyzate of Reference Method 4 | |
| purified water | 89.3 |

EXAMPLE 18

Hair rinse was prepared in accordance with the conventional method with the following ingredients.

| | |
|---|---|
| dialkyl dimethyl ammonium chloride solution | 2.0 (%) |
| cetyl alcohol | 1.0 |
| polyoxyethylene stearyl ether | 1.0 |
| 1,3-butylene glycol | 3.0 |
| hydroxyethylenecellulose hydroxypropyl trimethyl ammonium chloride ether | 0.2 |
| fraction A of milk protein | 4.5 |
| hydrolyzate of Reference Method 3 | |
| purified water | 88.3 |

EXAMPLE 19

Hair rinse was prepared in accordance with the conventional method with the following ingredients.

| | |
|---|---|
| dialkyl dimethyl ammonium chloride solution | 2.0 (%) |
| cetyl alcohol | 1.0 |
| polyoxyethylene stearyl ether | 1.0 |
| 1,3-butylene glycol | 3.0 |
| hydroxyethylenecellulose hydroxypropyl trimethyl ammonium chloride ether | 0.2 |
| fraction B of milk protein | 4.5 |
| hydrolyzate of Reference Method 3 | |
| purified water | 88.3 |

EXAMPLE 20

Hair shampoo was prepared in accordance with the conventional method with the following ingredients.

| | |
|---|---|
| triethanolamine lauryl sulfate solution | 15.0 (%) |
| 1,3-buthylene glycol | 2.0 |
| ethyleneglycol monostearate | 1.5 |
| fraction E of milk protein | 5.0 |
| hydrolyzate of Reference Method 4 | |

-continued

| purified water | 76.5 |

EXAMPLE 21

Hair shampoo was prepared in accordance with the conventional method with the following ingredients.

| triethanolamine lauryl sulfate solution | 15.0 (%) |
| 1,3-buthylene glycol | 2.0 |
| ethyleneglycol monostearate | 1.5 |
| fraction F of milk protein hydrolyzate of Reference Method 4 | 5.0 |
| purified water | 76.5 |

EFFECTS OF THE INVENTION

The effects of the present invention are as follows:
1) The milk protein hydrolyzate having a property to activate proliferation of human cutaneous cells and not having antigenicity of the milk protein can be provided in higher yield.
2) The fraction of milk protein hydrolyzate having a property to activate proliferation of human cutaneous cells and not having antigenicity of the milk protein can be provided in higher yield.
3) Hair treating compositions having reliable effects for prevention or recovery from damaged hairs, improvement in softness of hairs, smoothness after hair caring, brightness of hairs and recovery from dry and roughened hairs can be provided.
4) The skin treating compositions having reliable effects for prevention or recovery from roughened skin, improvement in smoothness of the skin, improvement in regularity of ridges and furrows of the skin, improvement in elasticity of the skin, improvement in softness of the skin and protection of the skin can be provided.

TABLE 1

| Milk Protein | Casein | | | Whey Protein | | Casein |
|---|---|---|---|---|---|---|
| (decomposition rate) | 21% | 32% | 41% | 30% | 41% | 17% |
| Sample | A | B | C | D | E | F |
| Quantity of Aromatic Amino Acids in the Whole Amino Acids (mg/g) | 81.3 | 73.9 | 59.6 | 65.8 | 55.7 | 76.0 |
| Quantity of Free Aromatic Amino Acids in the whole amino acids (mg/g) | 24.9 | 41.8 | 53.9 | 42.4 | 50.3 | 1.5 |
| Ratio of Free Aromatic Amino Acids to the Whole Aromatic Amino Acids (%) | 30.6 | 56.6 | 90.4 | 64.4 | 90.3 | 2.0 |

TABLE 2

| Cell | Epithelial Cell | | | Fibroblast | | |
|---|---|---|---|---|---|---|
| (μg/ml) | Sample C | B. placenta | Sample F | Sample C | B. placenta | Sample F |
| 0 | 14693 | 14693 | 14693 | 2538 | 2538 | 2538 |
| 1 | 15428 | 15575 | 13958 | 2919 | 2436 | 2539 |
| 10 | 16603 | 14252 | 14987 | 2944 | 2107 | 2259 |
| 100 | 15722 | 15134 | 14105 | 2792 | 1726 | 2614 |

Note:
unit is cpm

TABLE 3

| | Products for the Skin | | | |
|---|---|---|---|---|
| Evaluation Items | Skin Cream | Toilet Water | Cologne Water | Ointment for epidermis |
| Recovery from Roughened of Skin | +2.0 | +2.0 | +1.8 | +2.0 |
| Smoothening of the Skin | +1.0 | +1.0 | +1.8 | +1.8 |
| Regularity of ridges & furrows of the Skin | +1.0 | +1.0 | +1.8 | +0.8 |
| Elasticity of the Skin | +1.8 | +1.8 | +1.0 | +1.2 |
| Softness of the Skin | +1.2 | +1.0 | +1.0 | +1.2 |
| Protection of the Skin | +1.0 | +0.8 | +1.0 | +0.8 |

TABLE 4

| | Products for the hairs | | |
|---|---|---|---|
| Evaluation Items | Hair Treatment | Hair Rinse | Hair Shampoo |
| Recovery from Damaged Hairs | +1.8 | +2.0 | +1.8 |
| Softness of Hairs | +1.0 | +2.0 | +1.0 |
| Smoothness after Hair Caring | +1.0 | +1.8 | +1.8 |
| Recovery from Dry & Roughened Hairs | +1.8 | +1.8 | +1.8 |
| Brightness of Hairs | +1.0 | +1.0 | +0.8 |

TABLE 5

| Quantity Added (%) | Skin Cream | Hair Treatment |
|---|---|---|
| 0 | 0 | 0 |
| 0.01 | +0.8 | +0.6 |
| 0.05 | +1.0 | +1.0 |
| 0.1 | +1.2 | +1.0 |
| 1.0 | +1.8 | +1.6 |
| 5.0 | +2.0 | +1.8 |
| 10.0 | +2.0 | +2.0 |
| 20.0 | +2.0 | +2.0 |
| 30.0 | +0.2 | +0.2 |
| 50.0 | +0.2 | +0.2 |

TABLE 6

| | Quantity of Hydrolyzate to be Added (%) | | | |
|---|---|---|---|---|
| Products | 0 | 0.01 | 20.0 | 50.0 |
| Toilet Water | 0 | +1.0 | +2.0 | +0.2 |
| Cologne Water | 0 | +1.0 | +2.0 | +0.2 |
| Ointment for Epidamis | 0 | +1.0 | +2.0 | 0 |
| Hair Rinse | 0 | +1.0 | +2.0 | +0.2 |
| Hair Shampoo | 0 | +1.0 | +2.0 | +0.2 |

TABLE 7

| Milk Protein (elution peak) Fraction | Casein | | | | Whey Protein | | | |
|---|---|---|---|---|---|---|---|---|
| | 1st A | 2nd B | 3rd C | 4th D | 1st E | 2nd F | 3rd G | 4th H |
| Quantity of WA in the Fraction (mg/g) | 849 | 718 | 787 | 829 | 937 | 852 | 913 | 926 |
| Quantity of Ar in the Fraction (mg/g) | 4.7 | 17.9 | 374 | 544 | 5.0 | 24.8 | 425 | 593 |
| Quantity of Ar in WA (%) | 0.6 | 2.5 | 48 | 66 | 0.5 | 2.9 | 47 | 64 |

TABLE 8

| Quantity Added (µg/ml) | Epitherial Cells | | | | Fibroblasts | | | |
|---|---|---|---|---|---|---|---|---|
| | Frct. A | Fract. B | B. plcnt. | Smpl. I | Fract. A | Fract. B | B. plcnt. | Smpl. I |
| 0 | 14693 | 14693 | 14693 | 14693 | 2538 | 2538 | 2538 | 2538 |
| 1 | 17631 | 16456 | 15575 | 13958 | 2944 | 2995 | 2436 | 2539 |
| 10 | 18513 | 17485 | 14252 | 14987 | 2919 | 3705 | 2107 | 2259 |
| 100 | 15281 | 16603 | 15134 | 14105 | 2792 | 3325 | 1726 | 2614 |

TABLE 9

| | Products for the Skin and Sample Nos. | | | | | | | |
|---|---|---|---|---|---|---|---|---|
| | Skin Cream | | Toilet Water | | Cologne Water | | Oint. for epid. | |
| Evaluations Items | No. 8 | No. 9 | No. 10 | No. 11 | No. 12 | No. 13 | No. 14 | No. 15 |
| Recovery from Roughened of the skin | +2.0 | +1.8 | +2.0 | +1.8 | +2.0 | +1.8 | +2.0 | +1.8 |
| Smoothening of the Skin | +1.2 | +1.0 | +1.2 | +1.4 | +1.8 | +1.2 | +1.8 | +1.2 |
| Regularity of ridges & furrows of the Skin | +1.2 | +1.0 | +1.0 | +1.0 | +2.0 | +1.4 | +1.2 | +1.0 |
| Elasticity of the Skin | +1.8 | +0.8 | +1.8 | +1.8 | +1.8 | +1.4 | +1.8 | +1.0 |
| Softness of the Skin | +0.8 | +0.8 | +0.8 | +0.8 | +1.0 | +1.0 | +1.4 | +0.8 |
| Protection of the Skin | +0.8 | +0.8 | +1.0 | +1.0 | +1.0 | +1.0 | +0.8 | +0.8 |

TABLE 10

| | Products for the Hairs and Sample Nos. | | | | | |
|---|---|---|---|---|---|---|
| | Hair Treatment | | Hair Rinse | | Hair Shampoo | |
| Evaluation Items | No. 16 | No. 17 | No. 18 | No. 19 | No. 20 | No. 21 |
| Recovery from the Damaged Hairs | +2.0 | +1.8 | +2.0 | +1.8 | +1.8 | +1.8 |
| Softness of the Hairs | +1.2 | +1.0 | +2.0 | +1.4 | +1.2 | +1.0 |
| Smoothness after Hair Caring | +1.8 | +1.4 | +1.8 | +1.2 | +1.8 | +1.2 |
| Recovery from the Dry & Roughened Hairs | +1.4 | +1.4 | +2.0 | +1.4 | +1.4 | +1.4 |
| Brightness of the Hairs | +1.2 | +1.2 | +1.4 | +1.0 | +1.4 | +0.8 |

TABLE 11

| | Products and Sample Nos. | | | |
|---|---|---|---|---|
| | Skin Cream | | Hair Treatment | |
| Quantity Added | No. 8 | No. 9 | No. 16 | No. 17 |
| 0 | 0 | 0 | 0 | 0 |
| 0.01 | +0.8 | +0.4 | +0.6 | +0.4 |
| 0.05 | +1.0 | +0.8 | +1.0 | +0.4 |
| 0.1 | +1.4 | +1.0 | +1.2 | +0.8 |
| 1.0 | +1.8 | +1.4 | +1.8 | +1.4 |
| 5.0 | +2.0 | +1.8 | +2.0 | +1.8 |
| 10.0 | +2.0 | +1.8 | +2.0 | +1.8 |
| 20.0 | +2.0 | +1.8 | +2.0 | +1.8 |
| 30.0 | +0.1 | +0.1 | +0.1 | +0.1 |
| 50.0 | +0.1 | +0.1 | +0.1 | +0.1 |

TABLE 12

| Products | Sample | Quantity of Hydrolyzate to be Added (%) | | | | | |
|---|---|---|---|---|---|---|---|
| | | 0 | 0.01 | 1.0 | 20.0 | 30.0 | 50.0 |
| Toilet Water | No. 10 | 0 | +0.4 | +1.8 | +2.0 | +0.1 | +0.1 |
| | No. 11 | 0 | +0.4 | +1.4 | +1.8 | +0.1 | +0.1 |
| Cologne Water | No. 12 | 0 | +0.6 | +1.6 | +2.0 | +0.1 | +0.1 |
| | No. 13 | 0 | +0.4 | +1.4 | +1.8 | +0.1 | +0.1 |
| Ointment for Epidamis | No. 14 | 0 | +0.4 | +1.8 | +2.0 | +0.1 | +0.1 |
| | No. 15 | 0 | +0.4 | +1.6 | +1.8 | +0.1 | +0.1 |
| Hair Rinse | No. 18 | 0 | +0.6 | +1.8 | +2.0 | +0.2 | +0.1 |
| | No. 19 | 0 | +0.4 | +1.6 | +1.8 | +0.1 | +0.1 |
| Hair Shampoo | No. 20 | 0 | +0.4 | +1.4 | +1.8 | +0.2 | +0.2 |
| | No. 21 | 0 | +0.4 | +1.2 | +1.8 | +0.1 | +0.1 |

What is claimed is:

1. A milk-protein hydrolyzate obtained by the enzymatic hydrolysis of milk-protein, said hydrolyzate consisting of a mixture of peptides and free amino acids, said hydrolyzate having proliferation activating property on human cutaneous cells but not having antigenicity of the milk protein, said peptides having molecular weights less than 1000 daltons, said hydrolyzate having a free aromatic amino acid/total aromatic amino acid ratios of at least 90%; or a physiologically acceptable salt thereof.

2. A milk-protein hydrolyzate fraction obtained by fractionation of the milk-protein hydrolyzate of claim 1, said fraction consisting of a mixture of peptides and free amino acids, said fraction having proliferation activating property on human cutaneous cells but not having antigenicity of the milk-protein, said fraction containing aromatic amino acids in an amount of less than 5% by weight of total amino acids, or a physiologically acceptable salt thereof.

3. A cosmetic composition for application to the hair or skin comprising a cosmetically effective amount of the milk protein hydrolyzate according to claim 1 and a physiologically acceptable excipient.

4. A cosmetic composition for application to the hair or skin comprising a cosmetically effective amount of the milk protein hydrolyzate fraction according to claim 2 and a physiologically acceptable excipient.

* * * * *